United States Patent [19]

Crea

[11] Patent Number: 4,888,286
[45] Date of Patent: Dec. 19, 1989

[54] PRODUCTION OF GENE AND PROTEIN ANALOGS THROUGH SYNTHETIC GENE DESIGN USING DOUBLE STRANDED SYNTHETIC OLIGONUCLEOTIDES

[75] Inventor: Roberto Crea, Burlingame, Calif.

[73] Assignee: Creative BioMolecules, Inc., Hopkinton, Mass.

[21] Appl. No.: 30,244

[22] Filed: Mar. 24, 1987

Related U.S. Application Data

[63] Continuation of Ser. No. 577,130, Feb. 6, 1984, abandoned.

[51] Int. Cl.$^4$ ............... C12P 21/00; C12P 21/02; C12N 15/00
[52] U.S. Cl. .................... 435/172.3; 435/69.4; 435/320; 435/91; 935/9; 935/10; 935/11; 935/12
[58] Field of Search ............ 435/68, 70, 172.3, 320, 435/91; 935/1, 6, 10, 22, 23, 9, 11, 12

[56] References Cited

U.S. PATENT DOCUMENTS 4,359,535  11/1982  Pieczenik ..................... 435/317

FOREIGN PATENT DOCUMENTS 2007676  5/1979  United Kingdom ............. 103/52

OTHER PUBLICATIONS

Guillemin et al., 1982, "Growth Hormone-Releasing Factor from a Human Pancreatic Tumor . . . ", Science, V. 218, 585–587.
Maniatis et al., 1982, Molecular Cloning A Laboratory Manual, Cold Spring Harbor Lab., pp. 11–14.
Rinderknecht et al., 1978, "The Amino Acid Sequence of Human Insulin-Like Growth Factor I . . . ", J. Biol. Chem. V. 282, pp. 2769–2776.
Delbadie-McFarland et al., Proc Natl. Acad. Sci., U.S.A., V. 79, pp. 6409–6413, Jun., 1982.
Wallace et al., Nucl. Acid Res., V. 9, No. 15, 1981.
Messing et al., Nucleic Acid Research, V. 9, No. 2, 1981, pp. 309–321.
Goeddel et al., Nature, V. 287, No. 5781, pp. 411–416, Oct., 1980.
Goeddel et al., Nucleic Acid Research, V. 8, No. 18, pp. 4057–4074.
Goeddel et al., Nature, V. 281, No. 5732, pp. 544–548, Oct., 1979.
The Peptides, Academic Press, 1983, Chapter 1, Synthesis of Polypeptides by Recombinant DNA Methods, Wetzel et al.
Itakura et al., Science, V. 198, pp. 1056–1063, Dec., 1977, and UK 2,007,676A.
Wetzel et al., Biochemistry, V. 19, pp. 6096–6104, 1980.
Crea et al., Nucl. Acids Research, V. 8, No. 10, 1980, pp. 2331–2348.
Itakura, Chemical Synthesis of Genes, Elsevier Biomedical Press, Dec., 1982, pp. 442–445.
Crea et al., Proc. Natl. Acad. Sci., U.S.A., V. 75, No. 12, pp. 5765–5769, Dec., 1978.
Smith et al., Nucl. Acids Res., V. 10, No. 15, 1982, pp. 4467–4482.
Scientific American, Feb., 1983, Synthetic Vaccines, pp. 66–74.
Atassi et al., Proc. Natl. Acad. Sci., U.S.A. No. 80, pp. 840–844, Feb., 1983.
Backman et al., "Construction of Plasmids Carrying the cI Gene of Bacteriophage $\lambda$", 73 Proc. Natl. Acad. Sci. U.S.A. 11: 4174–4178 (1976).
Heffron et al., "In Vitro Mutagenesis of a Circular (List continued on next page.)

Primary Examiner—Robin L. Tieskin
Attorney, Agent, or Firm—Lahive & Cockfield

[57] ABSTRACT

Methods and compositions are provided for the production of gene mutations and protein analogs using synthetic gene design and double-stranded synthetic oligonucleotide cassettes. The disclosure provides synthetic structural genes, synthetic double-stranded oligonucleotide cassettes and methods for the creation of synthetic gene analogs and polypeptide analogs by shortening or altering the native amino acid sequence.

11 Claims, 2 Drawing Sheets

OTHER PUBLICATIONS

DNA Molecule by Using Synthetic Restriction Sites", 75 *Proc. Natl. Acad. Sci. U.S.A.* 12: 6012–6016.

Wilkinson et al., "A Large Increase in Enzyme-Substrate Affinity by Protein Engineering", *Nature*, 307: 187–188 (1984).

Stahl et al., "Replacement of the *Bacillus subtillus* Subtilisin Structural Gene . . . ," 158 *J. of Bacteriology*, 2:411–418 (1984).

Tatchell et al., "In Vitro Mutation Analysis of the Mating-Type Locus in Yeast", *Cell*, 27: 25–35 (1981).

Sakonju et al., "A control Region in the Center of the 5S RNA Gene Directs Specific Initiation of Transcription: I. The 5' Border of the Region", *Cell*, 19:13–25 (1980).

Winter et al., "Redesigning Enzyme Structure by Site-Directed Mutagenesis: Tyrosyl tRNA Synthetase and ATP Binding", *Nature*, 299:756–758 (1982).

GROWTH HORMONE-RELEASING FACTOR SYNTHETIC GENE

```
           1   2   3   4   5   6   7   8   9  10  11  12  13  14  15  16  17  18  19  20  21  22
          MetTyrAlaAspAlaIlePheThrAsnSerTyrArgLysValLeuGlyGlnLeuSerAlaArgLysLeu
AATTCATGTACGCAGACGCTATCTTTACTAACTCTTACCGTAAAGTTCTGGGCCAGCTGTCTGCACGCAAGCTT
    GTACATGCGTCTGCGATAGAAATGATTGAGAATGGCATTTCAAGACCCGGTCGACAGACGTGCGTTCGAA
EcoRI                                                      PvuII         HindIII 23  24  25  26  27  28  29  30  31  32  33  34  35  36  37  38  39  40  41  42  43  44 Stop
LeuGlnAspIleMetSerArgGlnGlnGlyGluSerAsnGlnGluArgGlyAlaArgLeu
CTGCAGGATATCATGTCTAGACAGCAGGGCGAATCTAACCAGGAGCGTGGCGCCCGTGCACGCCTGTAG
GACGTCCTATAGTACAGATCTGTCGTCCCGCTTAGATTGGTCCTCGCACCGCGGGCACGTGCGGACATCCTAG
PstI   EcoRV  XBaI                             NarI   HgiAI        BamHI
```

FIG. 1

```
            1   2   3   4   5   6   7   8   9  10  11  12  13  14  15  16  17  18  19  20  21  22
           Met Gly Pro Glu Thr Leu Cys Gly Ala Glu Leu Val Asp Ala Leu Gln Phe Val Cys Gly Asp Arg Gly
     AATTCATGGGTCCGGAAACTCTGTGCGGCGCCGAGCTGGTCGACGCTCTGCAGTTCGTTTGCGGTGACCGTGGT
         GTACCCAGGCCTTTGAGACACGCCGCGGCTCGACCAGCTGCGAGACGTCAAGCAAACGCCACTGGCACCA
     EcoRI                    NarI                            PstI 23  24  25  26  27  28  29  30  31  32  33  34  35  36  37  38  39  40  41  42  43  44  45  46  47
           Phe Tyr Phe Asn Lys Pro Thr Gly Tyr Gly Ser Ser Arg Arg Ala Pro Gln Thr Gly Ile Val Asp Glu Cys
     TTCTACTTCAACAAACCGACTGGTTACGGATCCTCTCTAGAACGTGCTCCGCAGACTGGTATCGTCGACGAATGC
     AAGATGAAGTTGTTTGGCTGACCAATGCCTAGGAGAGATCTGCACGAGGCGTCTGACCATAGCAGCTGCTTACG
                                 BamHI        XbaI 48  49  50  51  52  53  54  55  56  57  58  59  60  61  62  63  64  65  66  67  68  69  70
           Cys Phe Arg Ser Asp Leu Arg Leu Met Glu Tyr Cys Ala Pro Leu Lys Pro Ala Lys Ser Ala
     TGCTTCAGATCTTGCGACCTGCGTCGCCTGATGGAGTACTGCGCACCGCTGAAACCGGCTAAATCTGCTTGA
     ACGAAGTCTAGAACGCTGGACGCAGCGGACGCAGCTCATGACGCGTGGCGACTTTGGCCGATTTAGACGAACTTCGA
           BglII                 XhoI      MstI                              HindIII
```

FIG. 2

PRODUCTION OF GENE AND PROTEIN ANALOGS THROUGH SYNTHETIC GENE DESIGN USING DOUBLE STRANDED SYNTHETIC OLIGONUCLEOTIDES

This application is a continuation of application Ser. No. 577,130 filed 2/6/84, now abandoned.

TECHNICAL FIELD

This invention relates generally to methods and compositions for the alteration of DNA sequences. More particularly, the invention relates to methods and compositions for altering synthetic genes and producing polypeptide analogs by enzymatic digestion and insertion of double-stranded oligonucleotide fragments.

BACKGROUND ART

The numerous polypeptides which make up living organisms and their biochemical constituents are the expression products of the information contained in deoxyribonucleic acid (DNA). This information is coded by the order of the nucleic acid basis on the linear DNA sequence. The four bases, adenine (A), thymine (T), cytosine (C) and guanine (G), are arranged in a linear sequence as a single chain of DNA. Each triplet of bases, called a codon, encodes for a single amino acid.

With the advent of recombinant DNA technology, exemplified by the seminal work of Cohen and Boyer (U.S. Pat. No. 4,237,224), it became possible to introduce foreign genes into microorganisms and regulate the level of their expression. The cutting and splicing of DNA to prepare hybrid DNA sequences has been termed recombinant DNA (rDNA). This work relies on the discovery that restriction endonucleases (REN) recognize particular sites on a DNA sequence and cleave the DNA within these sites to produce predictable breaks in a sequence of DNA. REN sites have now been used in a variety of procedures to obtain expression of structural genes in foreign organisms.

To prepare recombinant DNA containing the appropriate elements to express foreign genes in a host cell, one normally purifies mRNA from tissues which express the desired polypeptide. The structural gene DNA may be reconstructed from the mRNA sequence by the enzyme reverse transcriptase, which has been isolated from an avian retrovirus. This complementary DNA (cDNA) can be digested with the REN, which cleave the cDNA at precisely defined sequences. This cDNA fragment is then typically cloned into an extrachromosomal DNA sequence which replicates autonomously, called the plasmid. The known techniques which have been employed generally involve naturally occurring restriction sites to construct the recombinant plasmids, or the introduction of short single-stranded oligonucleotide sequences followed by the completion of the double-stranded DNA using, e.g. DNA polymerase.

Many of the techniques using synthetic DNA oligonucleotides and restriction sites have been reviewed in R. Wetzel and D. V. Goeddel, "Synthesis of Polypeptides By Recombinant DNA Methods", from The Peptides, Academic Press, Inc., 5:1 (1983). Gene editing techniques have been used to alter the aminoterminal portion of interferon genes. The new genes have translational start codons immediately before the codon for the first amino acid of the mature protein, rather than at the beginning of the signal paptede coding region as occurs in the native gene (Goeddel, D. V., et. al., Nature 287:411 (1980); Goeddel, D. V., et. al., Nucl. Acid Res., 8:4057 (1980)). A similar "semi-synthesis" approach has been used to construct a gene coding for human growth hormone. A synthetic DNA fragment containing an ATG codon and the sequence for the first 23 amino acids of hGH was ligated to the remainder of the gene, which had been produced by the cDNA method (Goeddel, D. V., et. al., Nature 281:544 (1979)). This resulted in a gene that would direct the expression of mature hGH, instead of the pre-hormone.

Hybrid genes of interferon have also been constructed using REN sites common to two homologous genes (Weck, et. al., Nucl. Acids Res., 9:6153 (1981)).

In addition to these synthetic and semi-synthetic procedures for changing DNA sequences, internal mutations have been achieved randomly by chemical agents or ultraviolet light, or in specific locations using single-stranded oligonucleotides (Wallace, R. B. et. al., Nucl. Acids Res. 9:3647 (1981); Dalbadie-McFarland, G. et. al., Proc. Natl. Acad. Sci. U.S.A. 79:6409 (1982)).

In addition to the above methods of creating synthetic or altered genes, altered proteins (polypeptides), termed analogs, have been created for numerous applications by chemical synthesis of the entire amino acid sequence of the analog. As an example of a series of protein analogs, there are numerous opiod analgesics based on the Leu-Enkephalin Pentapeptide, related to B-endorphin. These peptides termed dynorphins range from tridecapeptides to heptadecapeptides, as exemplified in U.S. Pat. No. 4,396,606.

Human pancreatic growth hormone-releasing factor (hpGRF) was first isolated, purified and sequenced as a 44 amino acid polypeptide which stimulated the secretion of immunoreactive growth hormone (Guillemin, R, et al., Science, 218:585–587 (1982)) Subsequently, a varient was isolated and purified from a pancreatic islet tumor. This hpGRF (hpGRF(1-40)-OH) was found to terminate at amino acid residue 40 of the previously determined sequence. This varient retained essentially full biological activity as did the varients hpGRF(1-40)-$NH_2$ and hpGRF(1-29)-$NH_2$ (Spiess, J. et al., Biochemistry, 21:6037–6040 (1982)).

The amino acid sequence of human Insulin-like Growth Factor I has been previously determined (Rinderknecht, E. and R. E. Humble, J. Biol. Chem., 253:2769–2776 (1978)). This polypeptide, isolated from serum, is a single chain polypeptide of 70 amino acid residues which displays sequence homology to proinsulin. The chemical synthesis of a 70 amino acid residue polypeptide is inefficient and time consuming using current techniques.

DISCLOSURE OF THE INVENTION

The present invention provides novel methods and compositions for the construction of synthetic gene and polypeptide analogs. In one aspect of the invention, the method of altering the sequence of double-stranded DNA within a structural gene comprises digesting said structural gene DNA sequence with a first restriction endonuclease having a first cleavage recognition site within said gene, digesting said structural gene DNA sequence with a second restriction endonuclease having a second cleavage recognition site proximate to said first site, whereby at least major and minor structural gene fragments are created, and ligating to said major gene fragment a synthetic double-stranded oligonucleotide having terminal complementary to said first and second cleavage sites.

In another aspect, this invention provides a hybrid structural gene capable of expressing a gene product comprising a first double-stranded DNA sequence from a structural gene, a double-stranded oligonucleotide fused thereto, which oligonucleotide contains a non-native based sequence, and a second double-stranded DNA sequence from said structural gene fused to said oligonucleotide, whereby a hybrid structural gene capable of expressing the native gene product or an analog gene product is formed.

A further aspect of the invention provides a method of altering the sequence of double-stranded DNA within a structural gene comprising digesting said structural gene DNA sequence with at least one restriction endonuclease having a cleavage recognition site within said gene, whereby an intermediate DNA fragment is removed from said structural gene, and replacing said intermediate DNA fragment with a double-stranded oligonucleotide capable of being ligated to the terminal of the structural gene, whereby the intermediate DNA fragment is replaced with said double-stranded oligonucleotide.

A still further aspect of the invention provides a synthetic structural gene capable of expressing a polypeptide gene product comprising a sequence of codons capable of expressing the amino acids of said gene product, which codons have been selected to provide a plurality of restriction endonuclease sites intermediate to the terminal ends of said structural gene. The invention also provides a double-stranded oligonucleotide sequence capable of replacing at least one native or synthetic codon in a double-stranded DNA sequence from a structural gene.

Also provided are polypeptide analogs of human pancreatic Growth Hormone-Releasing Factor and human Insulin-like Growth Factor.

A novel feature of this invention is the use of synthetic double-stranded oligonucleotide sequences which code for either the native gene product amino acids using non-native codons, or code for non-native amino acids to create a polypeptide analog gene product. The present invention can utilize native structural genes, provided restriction sites can be found which permit the replacement of a nucleotide sequence by a desired synthetic oligonucleotide, termed a cassette.

A preferred embodiment however is the use of a synthetic structural gene which provides a plurality of restriction endonuclease (REN) sites arranged so as to allow precisely controlled replacement of various subunits of the structural gene. The directed replacement or mutagenesis of structural gene sequences is believed to offer several advantages over the prior art methods of producing hybrid genes and peptide analogs. Because, in the preferred embodiment, the invention is practiced on a synthetic structural gene with numerous REN sites, mutations can be rapidly and efficiently introduced without effecting the basic configuration of the gene.

By engineering the changes at the level of the DNA sequence, precise peptide analogs can be constructed without the necessity of synthesizing the analog de novo. Because DNA is double-stranded, the complementarity between each strand allows for the precise location of replacement codons coding for desired amino acids. A polypeptide analog synthesized de novo requires complete synthesis to replace even a single amino acid. In addition, current technology does not permit the synthesis of polypeptides exceeding approximately 50 amino acid residues.

BRIEF DESCRIPTION OF THE DRAWINGS

FIG. 1 is a diagrammatic representation of a synthetic gene coding for human pancreatic Growth Hormone-Releasing Factor, including the amino acid sequence and the restriction endonuclease sites designed into the synthetic gene; and FIG. 2 is a diagrammatic representation of a synthetic gene coding for Insulin-like Growth Factor 1 including the amino acid sequence and the restriction endonuclease sites.

BEST MODE FOR PRACTICING THE INVENTION

The present invention discloses methods and compositions for the creation of novel DNA sequences and polypeptide analogs by the precise placement of carefully engineered mutations to the previous DNA sequence. The invention allows one to molecularly engineer DNA structural gene analogs with a view towards the production of novel peptide analogs useful as, e.g., drugs, enzymes and synthetic vaccines.

The invention can also be used to introduce changes into DNA regions other than actual structural genes, e.g., promoters and other regulatory regions where the ability to make systematic alterations in the DNA sequence can improve the efficiency of expression of any recombinant DNA expression vector.

By using available techniques for the sequencing of DNA, such as, for example, the technique of Maxam and Gilbert (Maxam, A. N. and W. Gilbert, Methods in Enzymology 67:499 (1980)) it is possible to rapidly and efficiently sequence native structural genes upon obtaining a complementary DNA (cDNA) copy. Once the sequence of the structural gene is known, sequences for restriction endonuclease (REN) sites can readily be determined and a rational plan developed for the engineering of analog structural genes and the resultant analog polypeptides. However, native structural genes often do not have many native REN sites, therefore they are less desirable as embodiments for the generation of analogs in accordance with the present invention.

As an alternative, the amino acid sequence of a native polypeptide gene product can be determined by known sequencing techniques, which are presently rapid and economical. Chemically synthesized DNA coding for a polypeptide having a known sequence can be prepared by selecting codons for each amino acid according to the genetic code. Generally, a synthetic double-stranded DNA structural gene is designed to be formed by the assembly of several DNA fragments, each synthesized separately. Part of the DNA fragments (oligonucleotides) comprise the upper strand and part the lower strands of DNA. The fragments of the respective strands preferably overlap such that the complementarity with opposite fragments promote their self assembly through hydrogen bonding. Following this assembly, the structural gene is completed by enzymatic ligation using, e.g., DNA ligase. When required, single-stranded regions can be filled in with appropriate complementary bases using, e.g., DNA polymerase.

The degeneracy of the genetic code permits substantial freedom in the choice of codons for any given amino acid sequence. In the past, codon choice has been guided by at least three considerations. First, codons and fragments were selected so as to avoid undue complementarity of one fragment with another which is different from the opposite one in the intended gene. Secondly, sequences rich in AT base pairs are disfavored to avoid premature termination of the transcription. Thirdly, at least the majority of the condons chosen are those preferred in the expression of microbial genes (see, e.g. Gouy and Gautier, Nucl. Acids Res. 10:7055–7074 (1982)).

However, additional criteria can be imposed for generating DNA sequences within the double-stranded DNA which can be recognized specifically by REN. This can be accomplished by a specific choice of codons for adjacent amino acids. For example when a native polypeptide contains the amino acid doublet lysine-leucine (Lys-Leu), one can select the coding sequence for the two amino acids among twelve combinations as dictated by the degenerate code. However, only one of the twelve combinations will code for the sequence corresponding to the recognition site for the REN Hind III. Therefore, by choosing the codon AAG for lysine and the codon CTT for leucine, one can create a specific recognition site within the structural gene DNA. Similarly, several couples of amino acids can be identified for which it is possible to select specific codons so that the resulting sequence will be a recognition site for a specific REN. See Table 1 for a representative list.

TABLE 1

| RESTRICTION ENDONUCLEASE RECOGNITION SITES AND AMINO ACID SEQUENCES | | |
|---|---|---|
| ENZYME | DNA SEQUENCE (5'-3') | AA1-AA2 |
| Hind III | A A G C T T | LYS—LEU |
| Bgl II | A G A T C T | ARG—SER |
| Cla I | A T C G A T | ILE—ASP |
| Ava III | A T G C A T | MET—HIS |
| Rvu I | A G T A C T | SER—THR |
| Stu I | A G G C C T | ARG—PRO |
| Mlu I | A C G C G T | THR—ARG |
| Nru I | T C G C G A | SER—ARG |
| Bal I | T G G C C A | TRP—PRO |
| Xba I | T C T A G A | SER—ARG |
| Asu II | T T C G A A | PHE—GLU |
| Mst I | T G C G C A | CYS—ALA |
| Aha III | T T T A A A | PHE—LYS |
| Eco RI | G A A T T C | GLU—PHE |
| Hpa I | G T T A A C | VAL—ASN |
| Bam HI | G G A T C C | GLY—SER |
| Kpn I | G G T A C C | GLY—THR |
| Sal I | G T C G A C | VAL—ASP |
| Sph I | G C A T G C | ALA—CYS |
| Sst I | G A G C T C | GLU—LEU |
| Eco RV | G A T A T C | ASP—ILE |
| Sna I | G T A T A C | VAL—TYR |
| Nar I | G G C G C C | GLY—ALA |
| Nae I | G C C G G C | ALA—GLY |
| Apa I | G G G C C C | GLY—PRO |
| Aat II | G A C G T C | ASP—VAL |
| BssH II | G C G C G C | ALA—ARG |
| Pvu II | C A G C T G | GLN—LEU |
| Pst I | C T G C A G | LEU—GLN |
| Xho I | C T C G A G | LEU—GLU |
| Sma I | C C C G G G | PRO—GLY |
| Pvu I | C G A T C G | ARG—SER |
| Sac II | C C G C G G | PRO—ARG |
| Xma III | C G G C C G | ARG—PRO |
| Avr II | C C T A G G | PRO—ARG |
| Nco I | C C A T G G | PRO—TRP |
| Nde I | C A T A T G | HIS—MET |

Other REN sites of interest are disclosed in the literature, including, e.g. Roberts, R. J., Nucl. Acids Res. 10:r117–r14 (1982).

The design strategy employed in constructing the following synthetic gene specific embodiments was, in each case, based on a known amino acid sequence. Initially all possible codons were arranged using the Stanford code, which indicates potential alternative bases which can replace the original sequence and preserve the amino acid specificity.

Secondly, the codon choice was restricted to E. coli codon preferences, to facilitate greater expression in a E. coli system. However this criterion may be compromised to include more REN sites, or it can be modified or eliminated where appropriate for other production systems and where the level of expression appears to be independent of natural codon preferences.

Thirdly, the codons were selected in accordance with the previously described REN site selection, while avoiding sites which were present in a plasmid of choice or which had already been selected for previous incorporation into the synthetic genes. That is, by selecting a first REN site it is generally preferable to eliminate subsequent use of that REN site in the same gene. In addition it is generally desirable to eliminate sites for internal sequence of the synthetic gene which will be used at the gene terminal to clone the gene into the plasmid of choice.

Finally, the REN sites are spaced so as to avoid excessive overlap; generally sites are spaced between 10 and 40 bases apart. However, in particular applications a synthetic gene can be constructed which will enrich for REN sites to provide for more efficient generation of analogs of the gene.

In a long amino acid sequence, e.g. polypeptide human pancreatic Growth Hormone-Releasing Factor (hpGRF, 44 amino acids) and Insulin-like Growth Factor-1 (IGF 1, 70 amino acids), it is possible to identify several amino acid doublets among those disclosed in Table 1. By assigning the appropriate codons, one can create an array of restriction endonuclease sites throughout a synthetic gene. In the case of hpGRF (see FIG. 1) several useful REN sites were designed within the gene. A synthetic gene coding for IGF 1 has been constructed which also contains several useful REN sites (see FIG. 2). A restriction enzyme site can be termed "useful" when its frequency in the gene and cloning plasmid are very low. Ideally, only single sites will be selected in order to facilitate specific cleavage within the gene sequence.

A chemically synthesized gene having a large number of REN sites offers several advantages in constructing gene analogs, introducing specific mutations in gene sequence, and constructing genes having deletions of several partial sequences.

In the first two areas, the presence of adjacent or proximate REN sites allows for the cleavage of gene fragments and their replacement with synthetic new oligonucleotides, termed cassettes. This is accomplished with REN digestions with appropriate enzymes, followed by ligating the cassette using its previously designed complementary terminal. Thus, gene analogs can be created by replacing the original sequence between two restriction endonuclease sites with double-stranded cassettes which code for, e.g., different amino acids. For example, in the case of the hpGRF, the internal aino acid methionine (Met) at position 27 (see FIG. 1) is coded by the triplet ATG. This can be changed into another condon, such as e.g., CTG (which codes for Leu) by digesting the gene with the restriction enzymes Pst I and Xba I and replacing the small DNA fragment generated with a double-stranded DNA fragment which has been chemically synthesized.

Alternatively, the codon ATG can be replaced with codons which code for the amino acids isoleucine or valine.

This double-stranded DNA cassette is designed to allow ligation to the REN sites used in digestion, and therefore can have either cohesive terminal or can be blunt ended. Additionally, it is not necessary to restrict the selection of REN sites for digestion to those most closely bounding the region which is desirably to be altered. For example, in FIG. 1 it is seen that the sites Eco RV and Hind III can be used in conjunction with Xba I to provide digestion for cassette insertion. Less desirably, REN site Pvu II could also be used in conjunction with Xba I. Using, for example, the sites Pst I and Xba I, a cassette is designed of the following form, to provide replacements for the ATG codon at position 27 of hpGRF:

Wherein X, Y, and Z are chosen to provide a codon which codes for any amino acid except Met and X', Y' and Z' are the complementary bases to the selected X, Y and Z. In the particular example provided below, the synthetic cassette contains the codon CTG instead of ATG. Thus, the presence of REN sites placed along the synthetic gene sequence permits the generation of any number of gene analogs.

Another important aspect of the numerous useful REN sites in a gene sequence is the opportunity to delete certain regions of a DNA sequence without affecting the remaining structure. For example, in the case of the IGF 1 gene, a cleavage with the enzyme Mst I would eliminate the last portion of the gene. A double digestion with Xba I and Sal I would eliminate the central part of the gene. A digestion with Nar I (or Pst I) would eliminate the leading sequence of the same gene. Other combinations of REN digestion provide a method of recombining fragments of the gene into a new gene coding for a distinct polypeptide gene product provided that the fragments are arranged in correct reading frame and initiation and termination codons are provided as required by a synthetic oligonucleotide.

Thus the synthetic gene analogs find use in the production of polypeptide analogs by genetic engineering methods. The importance of these polypeptide analogs is well recognized. Analogs of, for example, hpGRF and IGF 1 could potentially be more effective than the original polypeptides for theraputic use with human or animals. Polypeptide analogs can be constructed which provide minor modifications in sequence, at the same time eliminating undesirable side effects in diagnostic and therapeutic use. In addition, such polypeptide analogs generated by rDNA provide for the determination of antigenic sites along the polypeptide. Thus they are useful to generate novel and efficient synthetic vaccines.

It is generally assumed that restriction enzyme digests will be made with the synthetic structural gene while it is contained within a plasmid. This would result in the production of a limited number of fragments with a single major fragment containing both the N-terminal sequence and the C-terminal sequence of the structural gene at opposite ends of the linear sequence containing the plasmid DNA. The minor segment produced by this digestion will contain internal structural gene sequence codons up to the limits defined by the boundaries of the chosen REN sites. Alternatively, restriction enzyme digests can be made with the structural gene in solution, thereby increasing the number of useful sites, as the sites contained in the plasmid need not be eliminated during the design of the synthetic gene. However such digests in solution increase the number of fragments produced, due in part to self-polymerization. This increased number of fragments makes the fragments of interest more difficult to isolate and purify and therefore decreases the efficiency of the creation of structural gene analogs.

The following examples are provided by way of illustration, rather than implying any limitation of the present invention.

EXPERIMENTAL

Samples presented here utilize generally synthetic structural genes and synthetic oligonucleotide sequence cassettes.

EXAMPLE 1

Growth Hormone-Releasing Factor Synthetic Gene

The amino acid sequence for the human pancreatic growth hormone releasing factor (hpGRF) peptide has been determined (Guillemin, R., et. al., Science 218:585 (1982)). Based on the 44 amino acid sequence, and the design criteria discussed previously, 22 oligonucleotides were synthesized by the solid-phase phosphotriester method (Crea, R. and T. Horn, Nucl. Acids Res., 8:2331-2348 (1980)). Generally oligonucleotides are synthesized by adding mononucleotides, dinucleotides or trinucleotides to a mononucleotide immobilized on a solid support. The oligonucleotide is thus constructed by serial addition of the selected mono-, di-, and trinucleotides. In the present constructs, dinucleotides were used in preference to trinucleotides. These oligonucleotides cumulatively contain the DNA sequence for the synthetic hpGRF gene. (Crea, R. et al., Proc. Nat Acad. Sci. U.S.A. 75:5765-5769 (1978)).

The oligonucleotides used to construct the hpGRF synthetic gene were designed as indicated in Table 2.

TABLE 2

| | hpGRF OLIGONUCLEOTIDES 5'—3' | | |
|---|---|---|---|
| GRF 1: | A A T T C A T G T A C G C | 13-mer |
| 2: | A G A C G C T A T C T T T | " |
| 3: | A C T A A C T C T T A C C | " |
| 4: | G T A A A G T T C T G G G | " |
| 5: | C C A G C T G T C T G C A | " |
| 6: | C G C A A G C T T C T G C | " |
| 7: | A G G A T A T C A T G T C | " |
| 8: | T A G A C A G C A G G G C | " |
| 9: | G A A T C T A A C C A G G | " |
| 10: | A G C G T G G C G C C C G | " |
| 11: | T G C A C G C C T G T A G | " |
| GRF 12: | G C G T C T G C G T A C A T G | 15-mer |
| 13: | G T T A G T A A A G A T A | 13-mer |
| 14: | C T T T A C G G T A A G A | " |
| 15: | A G C T G G C C C A G A A | " |
| 16: | C T T G C G T G C A G A C | " |
| 17: | T A T C C T G C A G A A G | " |
| 18: | T G T C T A G A C A T G A | " |
| 19: | A G A T T C G C C C T G C | " |
| 20: | C A C G C T C C T G G T T | " |
| 21: | C G T G C A C G G G C G C | " |
| 22: | G A T C C T A C A G G | 11-mer |

Each oligonucleotide was purified by ion exchange and reverse HPLC in accordance with Crea, et al., supra. Thereafter the size of the fragments was verified by polyacrylamide gel electrophoresis.

The hpGRF gene was then constructed from the 22 purified oligonucleotides by a series of ligation steps as outlined in Crea, et al., supra; Wetzel, R., et al., Biochemistry, 19:6096–6104 (1980). Generally, $^{32}$p-labeled oligomers were built into the hpGRF gene by a series of T$_4$ DNA ligase - catalyzed reactions using the complementarity of overlapping fragments to insure proper ordering. Since fragment No. 1 and No. 22 contain restriction site sequences, they are self-complementary and could polymerize during the ligation reaction; thus they were used in their unphosphorylated form. The final ligation product was partially purified by electrophoresis on a 10% polyacrylamide slab gel and elution of the region between 130 and 150 base pairs.

The full length hpGRF gene, flanked by an EcoRI site and a BamHI site was cloned into a plasmid vector and amplified in E. coli.

EXAMPLE 2

Polypeptides the size of hpGRF have been expressed by fusing the structural gene to a portion of the B-galactosidase structural gene to create fusion gene products. Thereafter, the polypeptide of interest is obtained by cleaving with CNBr. However this technique cannot be used if the polypeptide of interest contains an internal methionine.

From the amino acid sequence shown in FIG. 1, it can be seen that the native hpGRF polypeptide contains an internal methionine at amino acid position 27. Thus, this internal methionine presents an obstacle to the use of cyanogen bromide (CNBr) cleavage in preparing a functional gene product from a fusion gene product. Thus it was considered desirable to eliminate internal methionine, without altering the properties of the gene product.

A synthetic oligonucleotide cassette was constructed, bounded by the restriction enzyme sites Pst I and Xba I.

This cassette follows the general outline of the cassette designed discussed previously wherein X=C, Y=T and Z=G, as shown below:

After digesting the synthetic hpGRF gene with Pst I and Xba I, the major and minor fragments were separated by gel electrophoresis and the major fragment was religated with the synthetic cassette. Proper cassette orientation was preserved due to the lack of sequence homology between the Pst.I site and the Xba I site. The expression product was a growth hormone-releasing factor peptide analog which replaced the internal methionine at position 27 with a leucine residue, without substantially altering the properties of the gene and the ability to express a polypeptide analog.

EXAMPLE 3

Insulin-Like Growth Factor I

The synthetic gene for human insulin-like growth factor 1 (IGF-1) was designed to contain numerous useful REN sites (see FIG. 2).

The amino acid sequence of human Insulin-like Growth Factor 1 (having 70 amino acid residues) has been previously described (Rinderknecht, supra). The oligonucleotide sequences used to construct the complete IGF-1 gene in accordance with the procedure outlined in Example 1 are shown in Table 3.

TABLE 3

| IGF-1 OLIGONUCLEOTIDES (5'—3') | | |
|---|---|---|
| UPPER STRAND | | |
| IGF1-1: | A A T T C A T G G G T C C G | 14-mer |
| IGF1-2: | G A A A C T C T G T G C G G C | 15-mer |
| IGF1-3: | G C C G A G C T G G T C G A C | 15-mer |
| IGF1-4: | G C T C T G C A G T T C G | 13-mer |
| IGF1-5: | T T T G C G G T G A C C G | 13-mer |
| IGF1-6: | T G G T T T C T A C T T C | 13-mer |
| IGF1-7: | A A C A A A C C G A C T G G T | 15-mer |
| IGF1-8: | T A C G G A T C C T C T T C T | 15-mer |
| IGF1-9: | A G A C G T G C T C C G C A G | 15-mer |
| IGF1-10: | A C T G G T A T C G T C G | 13-mer |
| IGF1-11: | A C G A A T G C T G C T T | 13-mer |
| IGF1-12: | C A G A T C T T G C G A C | 13-mer |
| IGF1-13: | C T G C G T C C G C C T C G A G | 15-mer |
| IGF1-14: | A T G T A C T G C G C A | 12-mer |
| IGF1-15: | C C G C T G A A A C C G G | 13-mer |
| IGF1-16: | C T A A A T C T G C T T G A | 14-mer |
| LOWER STRAND | | |
| IGF1-17: | G A G T T T C C G G A C C C A T G | 17-mer |
| IGF1-18: | G C T C G G C G C C G C A C A | 15-mer |
| IGF1-19: | G C A G A G C G T C G A C C A | 15-mer |
| IGF1-20: | C C G C A A A C G A A C T | 13-mer |
| IGF1-21: | G A A A C C A C G G T C A | 13-mer |
| IGF1-22: | G T T T G T T G A A G T A | 13-mer |
| IGF1-23: | A T C C G T A A C C A G T C G | 15-mer |
| IGF1-24: | C A C G T C T A G A A G A G G | 15 mer |
| IGF1-25: | T A C C A G T C T G C G G A G | 15-mer |
| IGF1-26: | C A T T C G T C G A C G A | 13-mer |
| IGF1-27: | A G A T C T G A A G C A G | 13-mer |
| IGF1-28: | G A C G C A G G T C G C A | 13-mer |
| IGF1-29: | G T A C A T C T C G A G G C | 14-mer |
| IGF1-30: | T C A G C G G T G C G C A | 13-mer |
| IGF1-31: | G A T T T A G C C G G T T | 13-mer |
| IGF1-32: | A G C T T C A A G C A | 11-mer |

The IGF 1 gene was then constructed from the 32 oligonucleotides as detailed in Example 1.

The full length IGF 1 gene, flanked by an Eco RI site and a Hind III site was cloned into a plasmid vector and amplified in E. coli.

EXAMPLE 4

IGF 1 also contains an internal methionine amino acid residue at position 59. In FIG. 2 it is seen that this residue is flanked by REN sites for Xho I and Mst I. Thus in a manner analogous to Example 2, a synthetic cassette is created, bounded by the appropriate restriction sites, to replace the internal methionine with an amino acid residue which will not interfere with the biological activity of the IGF 1 polypeptide. An exemplary synthetic cassette is constructed as follows:

After digesting the synthetic IGF 1 gene with Xho I and Mst I, the major and minor fragments are separated and the major fragment religated with the synthetic cassette. Proper cassette orientation is preserved due to the lack of sequence homology between the Xho I site and the Mst I site as the Mst I site is blunt-ended. The expression product is an Insulin-like Growth Factor-1 polypeptide analog which replaces the internal methionine at position 59 with a leucine residue, without altering the properties of the gene and its ability to express a polypeptide analog.

Although the foregoing invention has been described in some detail by way of illustration and example for purposes of clarity of understanding, it will be obvious that certain changes and modifications may be practiced within the scope of the appended claims.

I claim:

1. A method of altering the nucleotide sequence of native double-stranded DNA encoding a protein, to prepare synthetic double-stranded DNA capable of expressing an analog of said protein, said method comprising the steps of:
   providing a synthetic double-standard DNA comprising a sequence of codons capable of expressing the amino acids of said protein and providing a plurality of non native restriction endonuclease sites;
   digesting said synthetic double stranded DNA with a first restriction endonuclease having a first cleavage recognition site within said double stranded DNA;
   digesting said synthetic double-stranded DNA with a second restriction endonuclease having a second cleavage recognition site proximate to said first site, whereby at least major and minor structural gene fragments are created; and
   ligating to said major genre fragment a synthetic double-stranded oligonucleotide having termini complementary to said first and second cleavage sites, said synthetic double-stranded oligonucleotide having a nucleotide sequence distinct from the nucleotide sequence of said minor structural gene fragment.

2. A method as recited in claim 1 wherein the major gene fragment comprises a plurality of fragments generated in said digestion steps, said method comprising the additional step of reassembling said plurality of fragments upon ligation with said synthetic double-stranded oligonucleotide.

3. A method as recited in claim 1 wherein the nucleotide sequence of said synthetic DNA defines a first restriction site specific to said first restriction endonuclease, and a second restriction site specific to said second restriction endonuclease which is distinct from said first restriction site.

4. A method as recited in claim 1 wherein said synthetic double-stranded DNA codes for the amino acid sequence identified as human pancreatic Growth Hormone-Releasing Factor.

5. A method as recited in claim 4 wherein said double-stranded oligonucleotide comprises a sequence designed to replace the internal methionine in said human pancreatic Growth Hormone-Releasing Factor polypeptide.

6. A method as recited in claim 5 wherein said double-stranded oligonucleotide comprises:

$$5'\text{-GGATATCXYZT-}3'$$
$$3'\text{-ACGTCCTATAGX'Y'Z'AGATC-}5'$$

wherein X, Y and Z are chosen to provide a codon for any amino acid residue except methionine and X', Y' and Z' are the appropriate complementary bases.

7. A method as recited in claim 1 wherein said synthetic double-stranded DNA codes for Insulin-like Growth Factor.

8. A method of altering the nucleotide sequence of double-standard DNA within a structural gene encoding a protein, to prepare synthetic double-stranded DNA capable of expressing an analog of said protein, said method comprising the steps of:
   providing a synthetic double-stranded DNA comprising a sequence of codons capable of expressing the amino acids of said protein and providing a plurality of non native restriction endonuclease sites;
   digesting said synthetic double-stranded DNA with at least one restriction endonuclease having a cleavage recognition site within said DNA, whereby an intermediate DNA fragment is removed from a terminus of said synthetic DNA; and
   replacing said intermediate DNA fragment with a synthetic double-stranded oligonucleotide capable of being ligated to the terminus of said synthetic DNA, whereby the intermediate DNA fragment is replaced with said synthetic double-stranded oligonucleotide.

9. A method as recited in claim 8 wherein said double-stranded oligonuclease contains an initiation codon.

10. A method as recited in claim 8 wherein said synthetic double-stranded oligonucleotide comprises a nucleotide sequence distinct from that of said intermediate DNA fragment.

11. A method as recited in claim 8 wherein said synthetic double-stranded oligonucleotide contains a termination codon.

* * * * *